US006376635B1

(12) United States Patent
Amako et al.

(10) Patent No.: US 6,376,635 B1
(45) Date of Patent: Apr. 23, 2002

(54) OLIGOSILOXANE AND METHOD OF PREPARING SAME

(75) Inventors: Masaaki Amako; Tadashi Okawa; Hiroji Enami; Masayuki Onishi, all of Chiba Prefecture (JP)

(73) Assignee: Dow Corning Toray Silicon Co., Ltd., Tokyo (JP)

( * ) Notice: Subject to any disclaimer, the term of this patent is extended or adjusted under 35 U.S.C. 154(b) by 0 days.

(21) Appl. No.: 09/702,638

(22) Filed: Nov. 1, 2000

(30) Foreign Application Priority Data

Nov. 15, 1999 (JP) .......................................... 11-324084
Nov. 15, 1999 (JP) .......................................... 11-324085

(51) Int. Cl.$^7$ ................................................ C08G 77/12
(52) U.S. Cl. ........................ 528/31; 556/450; 556/453; 556/455; 556/479; 528/15; 528/25
(58) Field of Search ............................. 528/15, 31, 25; 556/479, 450, 453, 455

(56) References Cited

U.S. PATENT DOCUMENTS 5,939,507 A  8/1999  Okawa ........................ 528/12

FOREIGN PATENT DOCUMENTS

| EP | 569304 A1 | * 10/1993 | |
|----|-----------|-----------|---|
| JP | 3-197486 | 8/1991 | ............ B01J/23/02 |
| JP | 3-287664 | 12/1991 | ............ C08K/5/54 |
| JP | 4-7305 | 1/1992 | ............ C08F/4/654 |
| JP | 5-70514 | 3/1993 | ............ C08F/4/654 |
| JP | 10-292047 | 11/1998 | ............ C07F/7/08 |
| JP | 11-217389 | 8/1999 | ............ C07F/7/08 |

* cited by examiner

Primary Examiner—Robert Dawson
Assistant Examiner—Marc S. Zimmer
(74) Attorney, Agent, or Firm—Larry Milco; Catherine Brown

(57) ABSTRACT

An oligosiloxane having the formula $(R^1O)_aSi(OSiR^2_2R^3)_{4-a}$ wherein $R^1$ is alkyl; each $R^2$ is independently selected from $C_1$ to $C_{10}$ monovalent hydrocarbyl free of aliphatic unsaturation; $R^3$ is hydrocarbly free of aliphatic unsaturation and having at least 11 carbon atoms; and a is 1, 2, or 3; and a method of preparing an alkoxy-functional oligosiloxane.

18 Claims, No Drawings

OLIGOSILOXANE AND METHOD OF PREPARING SAME

FIELD OF THE INVENTION

The present invention relates to an oligosiloxane and more particularly to an oligosiloxane containing both silicon-bonded alkoxy and monovalent hydrocarbyl groups, wherein each hydrocarbyl group is free of aliphatic unsaturation and has at least 11 carbon atoms. This invention also relates to a method of preparing an alkoxy-functional oligosiloxane.

BACKGROUND OF THE INVENTION

Silicon-bonded alkoxy-functional oligosiloxanes are disclosed in Japanese Laid Open (Kokai or Unexamined) Patent Application Numbers Hei 3-197486 (197,486/1991), Hei 4-7305 (7,305/1992), and Hei 5-70514 (70,514/1993). However, none of the references teach an alkoxy-functional oligosiloxane containing a monovalent hydrocarbyl group free of aliphatic unsaturation and having at least 11 carbon atoms.

Methods for preparing silicon-bonded alkoxy-functional oligosiloxanes are known. For example, Japanese Laid Open (Kokai or Unexamined) Patent Application Number Hei 3-197486 (197,486/1991) teaches the reaction of silanol-functional oligosiloxane or silane with silicon-bonded alkoxy-functional silane in the presence of the hydroxide or chloride of an alkali metal or alkaline-earth metal or in the presence of a basic metal salt. In addition, the reaction of silanol-functional silane and silicon-bonded alkoxy-functional silane in the presence of an amine compound is taught in Japanese Laid Open (Kokai or Unexamined) Patent Application Numbers Hei 4-7305 (7,305/1992) and Hei 5-70514 (70,514/1993). These methods, however, suffer from impaired yields of the desired oligosiloxane because they require the use of an unstable silanol-functional oligosiloxane or silane and because the silanol group in the starting oligosiloxane or silane undergoes intermolecular condensation with other silanol in the same reactant.

SUMMARY OF THE INVENTION

One object of the present invention is to provide novel oligosiloxanes containing both silicon-bonded alkoxy and monovalent hydrocarbyl groups, wherein each hydrocarbyl group is free of aliphatic unsaturation and has at least 11 carbon atoms. Another object of this invention is to provide a highly efficient method for synthesizing an alkoxy-functional oligosiloxane.

The present invention is directed to an oligosiloxane having the formula:

$$(R^1O)_a Si(OSiR^2_2 R^3)_{4-a}$$

wherein $R^1$ is alkyl; each $R^2$ is independently selected from $C_1$ to $C_{10}$ monovalent hydrocarbyl free of aliphatic unsaturation; $R^3$ is monovalent hydrocarbyl free of aliphatic unsaturation and having at least 11 carbon atoms; and a is 1, 2, or 3.

This invention is also directed to a method of preparing an oligosiloxane having the formula:

$$(R^1O)_a Si(OSiR^2_2 R^3)_{4-a}$$

comprising reacting an oligosiloxane having the formula:

$$(R^1O)_a Si(OSiR^2_2 H)_{4-a}$$

with a hydrocarbon containing 1 aliphatic double bond per molecule in the presence of a hydrosilylation catalyst, wherein $R^1$ is alkyl; each $R^2$ is independently selected from $C_1$ to $C_{10}$ monovalent hydrocarbyl free of aliphatic unsaturation; $R^3$ is monovalent hydrocarbyl free of aliphatic unsaturation and having at least 2 carbon atoms; and a is 1, 2, or 3.

The oligosiloxanes synthesized as described above are useful as surface treatment agents for inorganic fillers and as reactive oligosiloxanes capable of reacting with silanol-functional organopolysiloxanes and hydroxyl-functional organic resins. The method of the present invention affords silicon-bonded alkoxy-functional oligosiloxanes at high efficiencies.

DETAILED DESCRIPTION OF THE INVENTION

An oligosiloxane according to the present invention has the formula:

$$(R^1O)_a Si(OSiR^2_2 R^3)_{4-a}$$

wherein $R^1$ is alkyl; each $R^2$ is independently selected from $C_1$ to $C_{10}$ monovalent hydrocarbyl free of aliphatic unsaturation; $R^3$ is monovalent hydrocarbyl free of aliphatic unsaturation and having at least 11 carbon atoms; and a is 1, 2, or 3.

Examples of alkyl groups represented by $R^1$ include, but are not limited to, straight-chain alkyl such as methyl, ethyl, propyl, butyl, hexyl, and decyl; branched alkyl such as isopropyl, tert-butyl, and isobutyl; and cyclic alkyl such as cyclohexyl. $R^1$ preferably is $C_1$ to $C_4$ alkyl and more preferably is methyl or ethyl. $R^2$ is exemplified by straight-chain alkyl such as methyl, ethyl, propyl, butyl, hexyl, and decyl; branched alkyl such as isopropyl, tert-butyl, and isobutyl; cyclic alkyl such as cyclohexyl; aryl such as phenyl, tolyl, and xylyl; and aralkyl such as benzyl and phenethyl. $R^2$ is preferably $C_1$ to $C_4$ alkyl and more preferably is methyl or ethyl. $R^3$ is exemplified by straight-chain alkyl such as undecyl, dodecyl, tridecyl, tetradecyl, pentadecyl, hexadecyl, heptadecyl, octadecyl, nonadecyl, and eicosyl; branched alkyl such as 2-methylundecyl and 1-hexylheptyl; cyclic alkyl such as cyclododecyl; and aralkyl such as 2-(2,4,6-trimethylphenyl)propyl. $R^3$ is preferably straight-chain alkyl and more preferably is $C_{11}$ to $C_{20}$ straight-chain alkyl. The subscript a in the general formula under consideration can be 1, 2, or 3 and preferably is 3.

The oligosiloxanes of this invention are exemplified by the following compounds:

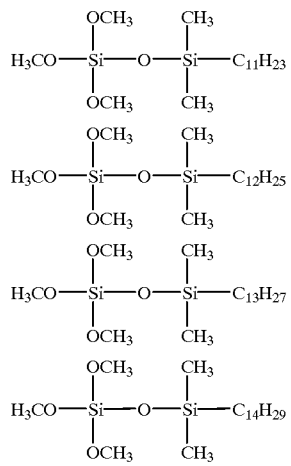

-continued

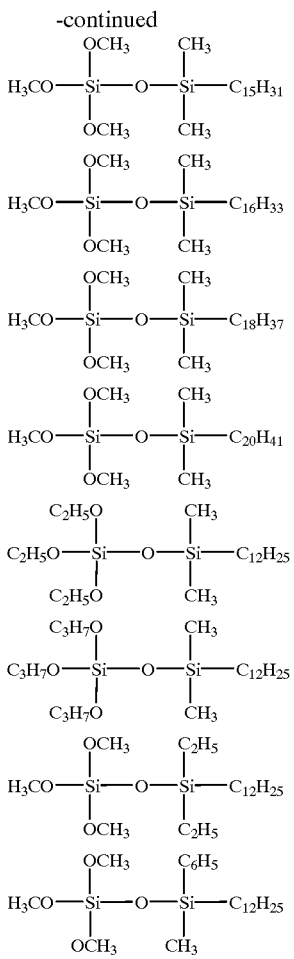

The oligosiloxanes described above, because they contain silicon-bonded alkoxy and monovalent hydrocarbyl groups, wherein each hydrocarbyl group is free of aliphatic unsaturation and has at least 11 carbon atoms, are useful as surface treatment agents for inorganic fillers and as reactive oligosiloxanes capable of reacting with silanol-functional organopolysiloxanes and hydroxyl-functional organic resins.

A method according to the present invention of preparing an oligosiloxane having the formula:

comprises reacting an oligosiloxane (A) having the formula:

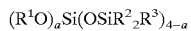

with a hydrocarbon (B) containing 1 aliphatic double bond per molecule in the presence of a hydrosilylation catalyst (C), wherein $R^1$, $R^2$, and subscript a are as defined and exemplified above, including the preferred embodiments thereof; $R^3$ is monovalent hydrocarbyl free of aliphatic unsaturation and having at least 2 carbon atoms. Preferably, the monovalent hydrocarbyl groups represented by $R^3$ have at least 11 carbon atoms.

Examples of hydrocarbyl groups represented by $R^3$ include, but are not limited to, straight-chain aliphatic hydrocarbyl such as ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, and nonadecyl; branched aliphatic hydrocarbyl such as 1-methylbutyl, 1-ethylpropyl, 1-ethylbutyl, 2-methylundecyl, and 1,1-dimethyldecyl; cyclic aliphatic hydrocarbyl such as cyclododecyl; and aromatic hydrocarbyl such as 2-(2,4,6-trimethylphenyl)propyl. $R^3$ is preferably straight-chain aliphatic hydrocarbyl (i.e., alkyl), more preferably is $C_2$ to $C_{20}$ straight-chain aliphatic hydrocarbyl, and most preferably is $C_{11}$ to $C_{20}$ straight-chain aliphatic hydrocarbyl.

The oligosiloxane (A) can itself be synthesized, for example, by the reaction of tetraalkoxysilane having the general formula $Si(OR^1)_4$, wherein $R^1$ is alkyl, with a disiloxane having the general formula $R^2_2HSiOSiR^2_2H$, wherein each $R^2$ is independently selected from $C_{11}$ to $C_{10}$ monovalent hydrocarbon groups free of aliphatic unsaturation, in the presence of a strong acid and a carboxylic acid.

The oligosiloxane (A) is exemplified by trialkoxysiloxydialkylsilanes such as trimethoxysiloxydimethylsilane, triethoxysiloxydimethylsilane, and tripropoxysiloxydimethylsilane; bis(dialkylsiloxy)dialkoxysilanes such as bis(dimethylsiloxy)dimethoxysilane, bis(dimethylsiloxy)diethoxysilane, bis(dimethylsiloxy)dipropoxysilane, and bis(dimethylsiloxy)dibutoxysilane; and tris(dialkylsiloxy)alkoxysilanes such as tris(dimethylsiloxy)methoxysilane, tris(dimethylsiloxy)ethoxysilane, tris(dimethylsiloxy)propoxysilane, and tris(dimethylsiloxy)butoxysilane.

A characteristic feature of the hydrocarbon (B) is that it contains 1 aliphatic double bond in each molecule. The molecular structure of component (B) is not critical and this component can be, for example, straight chain, branched, or cyclic. While the position of the aliphatic double bond in (B) is not critical, it is preferably present in molecular chain terminal position because of its higher reactivity in this position. Hydrocarbon (B) can be exemplified by straight-chain aliphatic hydrocarbons such as ethylene, propene, 1-butene, 2-butene, 1-pentene, 2-pentene, 1-hexene, 2-hexene, 3-hexene, 1-heptene, 1-octene, 1-nonene, 1-decene, 1-undecene, 1-dodecene, 1-tridecene, 6-tridecene, 1-tetradecene, 1-pentadecene, 1-hexadecene, 1-heptadecene, 1-octadecene, 1-nonadecene, and 1-eicosene; branched aliphatic hydrocarbons such as 2-methylundecene; cyclic aliphatic hydrocarbons such as cyclododecene; and aromatic hydrocarbons that contain an aliphatic double bond, such as 2-(2,4,6-trimethylphenyl) propene. The hydrocarbon (B) preferably is a straight-chain aliphatic hydrocarbon, more preferably is a $C_2$ to $C_{20}$ straight-chain aliphatic hydrocarbon, and most preferably is a $C_{11}$ to $C_{20}$ straight-chain aliphatic hydrocarbon.

The hydrosilylation catalyst (C) accelerates the addition in the preparative method under consideration of the silicon-bonded hydrogen in oligosiloxane (A) across the aliphatic double bond in hydrocarbon (B). This catalyst is exemplified by transition metal catalysts from Group VIII of the Periodic Table with platinum catalysts being particularly preferred. Said platinum catalysts are exemplified by chloroplatinic acid, alcohol solutions of chloroplatinic acid, olefin complexes of platinum, alkenylsiloxane complexes of platinum, and carbonyl complexes of platinum.

The molar ratio of component (B) to component (A) is not critical in the preparative method under consideration, but component (B) is preferably used at from 0.5 to 1.5 moles per 1 mole component (A) and more preferably is used in an amount equimolar with component (A).

The use of organic solvent in the preparative method under discussion is optional. When used, this organic solvent can be, for example, an aromatic such as benzene, toluene, or xylene; an aliphatic such as pentane, hexane, heptane, octane, or decane; an ether such as tetrahydrofuran, diethyl ether, or dibutyl ether; a ketone such as acetone or methyl ethyl ketone; an ester such as ethyl acetate or butyl acetate; or a chlorinated hydrocarbon such as carbon tetrachloride, trichloroethane, methylene dichloride, or chloroform.

The reaction temperature in the preparative method under discussion is also not critical and the reaction can be run at room temperature or with heating. When the reaction is run with heating, the reaction temperature is preferably from 50 to 200° C. The progress of the reaction can be followed by gas chromatographic analysis of the reaction solution or by monitoring the reaction system for the characteristic absorption of silicon-bonded hydrogen using, for example, infrared spectroscopic analysis or nuclear magnetic resonance analysis. The reaction can be regarded as finished when the characteristic absorption of the silicon-bonded hydrogen in the reaction solution has either disappeared or is no longer changing. After completion of the reaction, the desired oligosiloxane can be recovered by removal of the unreacted components and any organic solvent.

Examples of oligosiloxanes that can be prepared using the preceding method include:

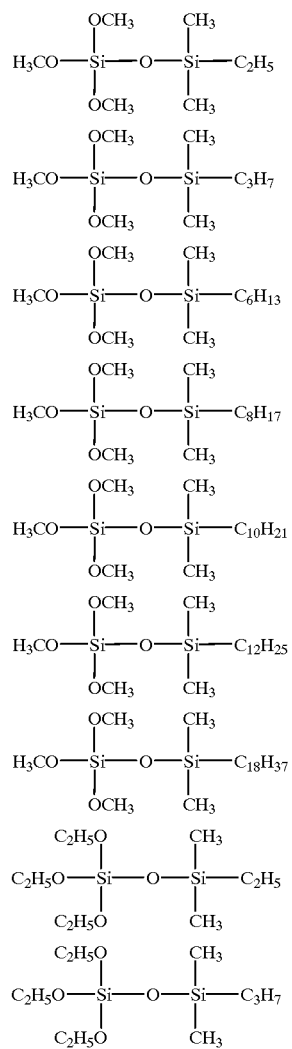

-continued

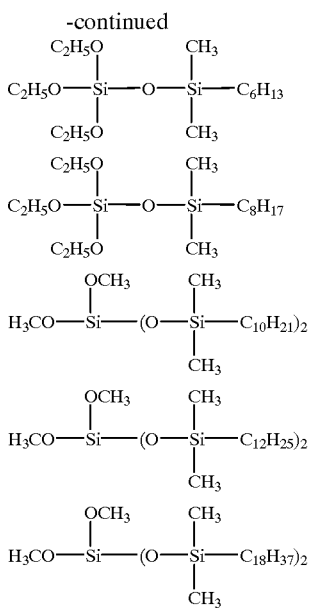

The inventive method for producing oligosiloxanes is characterized by the ability to synthesize silicon-bonded alkoxy-functional oligosiloxanes at high efficiencies. The oligosiloxanes afforded by the preparative method of this invention, because they contain silicon-bonded alkoxy groups, are useful as surface treatment agents for inorganic fillers and as reactive oligosiloxanes capable of reacting with silanol-functional organopolysiloxanes and hydroxyl-functional organic resins.

EXAMPLES

The oligosiloxanes according to this invention will be explained in greater detail through the working examples that follow. Physical properties of a cured organopolysiloxane composition were measured at 25° C.

Measurement of Penetration

The ¼ penetration was measured as described in JIS K 2220 on the curable organopolysiloxane composition after its introduction into a 50-mL glass beaker. Larger penetration values are indicative of a greater plasticity and better handling characteristics by the curable organopolysiloxane composition.

Determination of Moldability

The curable organopolysiloxane composition was sandwiched between 50-μm PET (polyethylene terephthalate) films so as to produce a thickness of 1 mm and curing was effected by heating for 30 minutes at 100° C. The ability to form a cured silicone sheet was observed when the PET films were then stripped off. The results were scored as follows: a score of + or good moldability was assigned when a sheet could be formed in an entirely unproblematic manner; a score of Δ or mediocre moldability was assigned when some portion could be formed into a sheet despite cohesive failure in some areas; a score of × or poor moldability was assigned when cohesive failure occurred over a large area and a sheet could not be formed.

Example 1

The following were introduced into a 1-liter four neck flask fitted with a stirrer, thermometer, condenser, and dropping funnel: 191.4 g (1.425 mol) 1,1,3,3-tetramethyldisiloxane, 474 g methyl orthosilicate, and 150 µL trifluoromethanesulfonic acid. The contents of the flask were heated to 50° C., at which point 85.56 g acetic acid was added dropwise over a period of 15 minutes. The flask was maintained at 50° C. after the completion of acetic acid addition and the reaction was monitored using gas chromatography (GLC). When disappearance of the GLC signal for acetic acid was confirmed, the flask was cooled to room temperature and 700 µL triethylamine was added for neutralization. Distillation then afforded 95 g of a fraction at 74–78° C./64 mmHg. Analysis of this fraction by GLC showed it to be composed (by integration ratio) of 90% oligosiloxane having the formula $(CH_3O)_3SiOSi(CH_3)_2H$, while the remaining 10% was oligosiloxane having the formula $(CH_3O)_2Si(OSi(CH_3)_2H)_2$.

Example 2

The following were placed in a 200-mL four neck flask fitted with a reflux condenser, thermometer, and dropping funnel: a spin bar, 50.0 g oligosiloxane whose synthesis is described in Example 1, and 6 µL of a toluene solution (platinum metal content=2 weight %) of a platinum/1,3-divinyltetramethyldisiloxane complex. The flask was then heated to 80° C., at which point 54.0 g 1-dodecene was added dropwise. The flask was maintained at 90° C. for 1 hour after the completion of 1-dodecene addition. This was followed by distillation of the low boilers at 150° C./10 mmHg, addition of 1 g active carbon, stirring for 1 hour at 80° C., and cooling to room temperature. The active carbon was then filtered off to yield 71.39 g of a colorless and transparent liquid. Analysis of this liquid by $^{13}$C-nuclear magnetic resonance spectroscopy ($^{13}$C-NMR) showed it to be trimethoxysiloxydimethyldodecylsilane with the formula $(CH_3O)_3SiOSi(CH_3)_2C_{12}H_{25}$. The purity of this siloxane by GLC was 90%. The remaining 10% was bis(dodecyldimethylsiloxy)dimethoxysilane with the formula $(CH_3O)_2Si(OSi(CH_3)_2C_{12}H_{25})_2$.

Example 3

The following were placed in a 100-mL three neck flask fitted with a reflux condenser, thermometer, and dropping funnel: a spin bar, 15.0 g oligosiloxane whose synthesis is described in Example 1, and 7 µL of a toluene solution (platinum metal content=2 weight %) of a platinum/1,3-divinyltetramethyldisiloxane complex. The flask was then heated to 90° C., at which point 30 g 1-octadecene was added dropwise. The flask was maintained at 90° C. for 1 hour after the completion of 1-octadecene addition. This was followed by distillation of the low boilers at 210° C./5 mmHg to give 24.7 g of a transparent, light-yellow liquid. Analysis of this liquid by $^{13}$C-NMR showed it to be trimethoxysiloxydimethyloctadecylsilane with the formula $(CH_3O)_3SiOSi(CH_3)_2C_{18}H_{37}$. The purity of this siloxane by GLC was 90%. The remaining 10% was bis(octadecyldimethylsiloxy)dimethoxysilane with the formula $(CH_3O)_2Si(OSi(CH_3)_2C_{18}H_{37})_2$.

Example 4

The following were placed in a 100-mL three neck flask fitted with a reflux condenser, thermometer, and dropping funnel: a spin bar, 7.08 g oligosiloxane whose synthesis is described in Example 1, and 10 µL of a toluene solution (platinum metal content=2 weight %) of a platinum/1,3-divinyltetramethyldisiloxane complex. The flask was then heated to 80° C., at which point 11.0 g 1-hexene was added dropwise. The flask was maintained at 80° C. for 1 hour after the completion of 1-hexene addition. This was followed by distillation of the low boilers at 90° C./12 mmHg to obtain 9.43 g trimethoxysiloxydimethylhexylsilane with the formula $(CH_3O)_3SiOSi(CH_3)_2C_6H_{13}$ in a purity of 90%. 2.28 g of this distillatively purified material was subjected to redistillation using a microtube oven; this resulted in the recovery of 1.49 g trimethoxysiloxydimethylhexylsilane with a purity by GLC of 99%.

Comparative Example 1

Trimethoxysiloxytrimethylsilane was synthesized in this comparative example according to the method described in Example 2 of Japanese Laid Open (Kokai or Unexamined) Patent Application Number Hei 3-197486. Thus, a spin bar, 59.35 g of a 50.7% cyclohexane solution of trimethylsilanol, 50.11 g methyl orthosilicate, and 0.4326 g calcium chloride were introduced into a 200-mL four neck flask fitted with a reflux condenser, thermometer, and dropping funnel. The flask was then heated at 60 to 70° C. for 7 hours. Analysis of the resulting reaction solution by GLC showed that there had been almost no condensation between the trimethylsilanol and methyl orthosilicate and that 25% of the starting trimethylsilanol had undergone silanol-to-silanol condensation with the production of hexamethyldisiloxane.

Example 4

This example concerns use of the inventive oligosiloxane as a surface treatment agent for inorganic filler. The property values reported in this application example were measured at 25° C.

A curable organopolysiloxane composition (I) was prepared by mixing the following to homogeneity in a double planetary mixer: 98 weight parts trimethylsiloxy-endblocked dimethylpolysiloxane in which a portion of the molecular chain terminals were endblocked by dimethylvinylsiloxy (this dimethylpolysiloxane had a viscosity of 930 mPa·s and contained 0.11 weight % vinyl), 0.54 weight part trimethylsiloxy-endblocked dimethylsiloxane-methylhydrogensiloxane copolymer (viscosity=4 mpa·s, Si-bonded hydrogen content=0.78 weight %), 450 weight parts spherical alumina powder with an average particle size of 10 µm, 450 weight parts irregularly shaped alumina powder with an average particle size of 2.2 µm, 5 weight parts oligosiloxane whose synthesis is reported in Example 1, and 0.2 weight part 1,3-divinyl-1,1,3,3-tetramethyldisiloxane complex of platinum in which the platinum concentration was 0.5 weight %.

For comparison, a curable organopolysiloxane composition (II) was prepared as above, but replacing the Example 1 oligosiloxane with the same amount of the oligosiloxane $(CH_3O)_3SiOSi(OCH_3)_3$.

Also for comparison, a curable organopolysiloxane composition (III) was prepared as above, but in this case omitting the Example 1 oligosiloxane. Table 1 reports the results of measurement of the properties of these curable organopolysiloxane compositions using the following methodologies.

TABLE 1

| curable organopolysiloxane composition | I | II | III |
|---|---|---|---|
| penetration (mm/10) | 80 | 25 | 20 |
| moldability | + | x | x |

The results in Table 1 show that use of the inventive oligosiloxane as a surface treatment agent for the inorganic filler gave a curable organopolysiloxane composition with good handling characteristics and good moldability. In contrast, use of the comparison oligosiloxane as a surface treatment agent for the inorganic filler (composition II) resulted in the formation of a sheet in which a portion of the alumina powder filler had aggregated into clumps. Finally, failure to use a treatment agent (composition III) resulted in aggregation of the alumina particles throughout the entire sheet and the inability to form a sheet with a smooth, even surface.

That which is claimed:

1. An oligosiloxane having the formula:

$$(R^1O)_a Si(OSiR^2{}_2 R^3)_{4-a}$$

wherein $R^1$ is alkyl; each $R^2$ is independently selected from $C_1$ to $C_{10}$ monovalent hydrocarbyl free of aliphatic unsaturation; $R^3$ is monovalent hydrocarbyl free of aliphatic unsaturation and having at least 11 carbon atoms; and a is 1, 2, or 3.

2. The oligosiloxane according to claim 1, wherein $R^1$ and $R^2$ are $C_1$ to $C_4$ alkyl.

3. The oligosiloxane according to claim 1, wherein $R^3$ is straight-chain alkyl.

4. The oligosiloxane according to claim 1, wherein $R^3$ is $C_{11}$ to $C_{20}$ staight-chain alkyl.

5. The oligosiloxane according to claim 1, wherein subscript a is 3.

6. A method of preparing an oligosiloxane having the formula:

$$(R^1O)_a Si(OSiR^2{}_2 R^3)_{4-a}$$

comprising reacting an oligosiloxane having the formula:

$$(R^1O)_a Si(OSiR^2{}_2 H)_{4-a}$$

with a hydrocarbon containing 1 aliphatic double bond per molecule in the presence of a hydrosilylation catalyst, wherein $R^1$ is alkyl; each $R^2$ is independently selected from $C_1$ to $C_{10}$ monovalent hydrocarbyl free of aliphatic unsaturation; $R^3$ is monovalent hydrocarbyl free of aliphatic unsaturation and having at least 2 carbon atoms; and a is 1, 2, or 3.

7. The process according to claim 6, wherein $R^1$ and $R^2$ are $C_1$ to $C_4$ alkyl.

8. The process according to claim 6, wherein the monovalent hydrocarbyl group represented by $R^3$ has at least 11 carbon atoms.

9. The process according to claim 6, wherein $R^3$ is straight-chain alkyl.

10. The process according to claim 9, wherein $R^3$ is $C_2$ to $C_{20}$ straight-chain alkyl.

11. The process according to claim 10, wherein $R^3$ is $C_{11}$ to $C_{20}$ straight-chain alkyl.

12. The process according to claim 6, wherein subscript a is 3.

13. The process according to claim 6, wherein the aliphatic double bond in the hydrocarbon is located at a terminal position.

14. The process according to claim 6, wherein the hydrocarbon is a $C_2$ to $C_{20}$ straight-chain aliphatic hydrocarbon.

15. The process according to claim 14, wherein the hydrocarbon is a $C_{11}$ to $C_{20}$ straight-chain aliphatic hydrocarbon.

16. The process according to claim 6, wherein the catalyst is a platinum catalyst.

17. The process according to claim 6, wherein the molar ratio of component (B) to component (A) is from 0.5 to 1.5.

18. The process according to claim 6, wherein the reaction is carried out at a temperature of from 50 to 200° C.

* * * * *